(12) United States Patent
Garcia et al.

(10) Patent No.: US 7,217,534 B2
(45) Date of Patent: May 15, 2007

(54) METHODS OF SCREENING APOPTOSIS MODULATING COMPOUNDS, COMPOUNDS IDENTIFIED BY SAID METHODS AND USE OF SAID COMPOUNDS AS THERAPEUTIC AGENTS

(75) Inventors: Alphonse Garcia, Montrouge (FR); Xavier Cayla, Rochecorbon (FR); Angelita Rebollo, Paris (FR); Veronica Ayllon, Alicante (ES); Aarne Fleischer, Paris (FR)

(73) Assignees: Institut Pasteur, Paris (FR); Consejo Superior de Investigaciones Cientificas, Madrid (ES); Centre National de la Recherche Scientifque, Paris (FR)

( * ) Notice: Subject to any disclaimer, the term of this patent is extended or adjusted under 35 U.S.C. 154(b) by 0 days.

(21) Appl. No.: 11/140,275

(22) Filed: May 31, 2005

(65) Prior Publication Data
US 2006/0040331 A1 Feb. 23, 2006

Related U.S. Application Data

(63) Continuation of application No. 10/934,513, filed on Sep. 7, 2004, which is a continuation of application No. PCT/EP03/02921, filed on Mar. 7, 2003, now abandoned.

(30) Foreign Application Priority Data
Mar. 7, 2002 (EP) .................................. 02290578

(51) Int. Cl.
G01N 33/00 (2006.01)
G01N 33/573 (2006.01)
C12N 5/16 (2006.01)
C12P 21/00 (2006.01)

(52) U.S. Cl. ..................... 435/7.23; 435/7.24; 435/7.4; 435/377.3

(58) Field of Classification Search ..................... None
See application file for complete search history.

(56) References Cited

U.S. PATENT DOCUMENTS 3,855,409 A 12/1974 Gordon et al.
2003/0049695 A1* 3/2003 Lu et al. ..................... 435/7.21

FOREIGN PATENT DOCUMENTS

WO WO 00/37088 6/2000
WO WO 01/10888 A1 2/2001
WO WO 01/48236 A1 7/2001

OTHER PUBLICATIONS

Urbano A, Gorgun G, Foss F. Mechanisms of apoptosis by the tyrphostin AG957 in hematopoietic cells. Biochem Pharmacol. Feb. 15, 2002;63(4):689-92.*

Gajate Consuelo et al: "The antitumor ether lipid ET-18-0CH3 induces apoptosis through translocation and capping of Fas/CD95 into membrane rafts in human leukemic cells." BLOOD, vol. 98, No. 13. Dec. 15, 2001, pp. 3860-3863, XP002233039 Dec. 25, 2001, ISSN: 006-4971.

Kabouridis Panagiotis S et al: "Cholesterol depletion disrupts lipid rafts and modulates the activity of mulitple singaling pathways in T lymphocytes." European Journal of Immunology., vol. 30, No. 3, Mar. 2000, pp. 954-963, XP002233040, issn:0014-2980.

Ayllon Veronica et al: "Protein phosphatase Ialpha is a Ras-activated Bad phosphatase that regulates interleukin-2 deprivation-induced apoptosis," EMBO (European Molecular Biology Organization) Jountal, vol. 19, n0. 10, May 15, 2000, pp. 2237-2246, XP002233041, ISSN: 0261-4189.

Robollo A et al: "The association of Aiolos transcription factor and Bc1-xL is involved in the control of apoptosis." Journal of Immunology (Baltimore, MD.: 1950) Unites States Dec. 1, 2001, vol. 167, No. 11, Dec. 1, 2001, pp. 6366-6373, XP002233042, ISSN: 0022-1767.

Simons K et al: "Lipid rafts and signal transduction" Nature reviews molecular cellbiology, Macmillan magazines, London, GB, vol. 1, No. 1, Oct. 2000, pp. 31-39, XP001006200.

* cited by examiner

Primary Examiner—Daniel M. Sullivan
Assistant Examiner—Laura McGillem
(74) Attorney, Agent, or Firm—Oblon, Spivak, McClelland, Maier & Neustadt, P.C.

(57) ABSTRACT

A method of screening cellular polypeptides for pro-apoptotic or anti-apoptotic activity in a cell of a particular cell-type by: (a) culturing cells of the particular cell-type under non apoptotic conditions and culturing cells of the particular cell-type under apoptotic conditions, and (b) determining subcellular localization of the cellular polypeptides in the cultured cells, wherein a localization of a cellular polypeptide in lipid rafts in cultured cells under non apoptotic conditions and a segregation of the cellular polypeptide from lipid rafts in cultured cells under apoptotic conditions is indicative that the cellular polypeptide has a pro-apoptotic or an anti-apoptotic activity in the particular cell-type.

18 Claims, 10 Drawing Sheets

Figure 1:
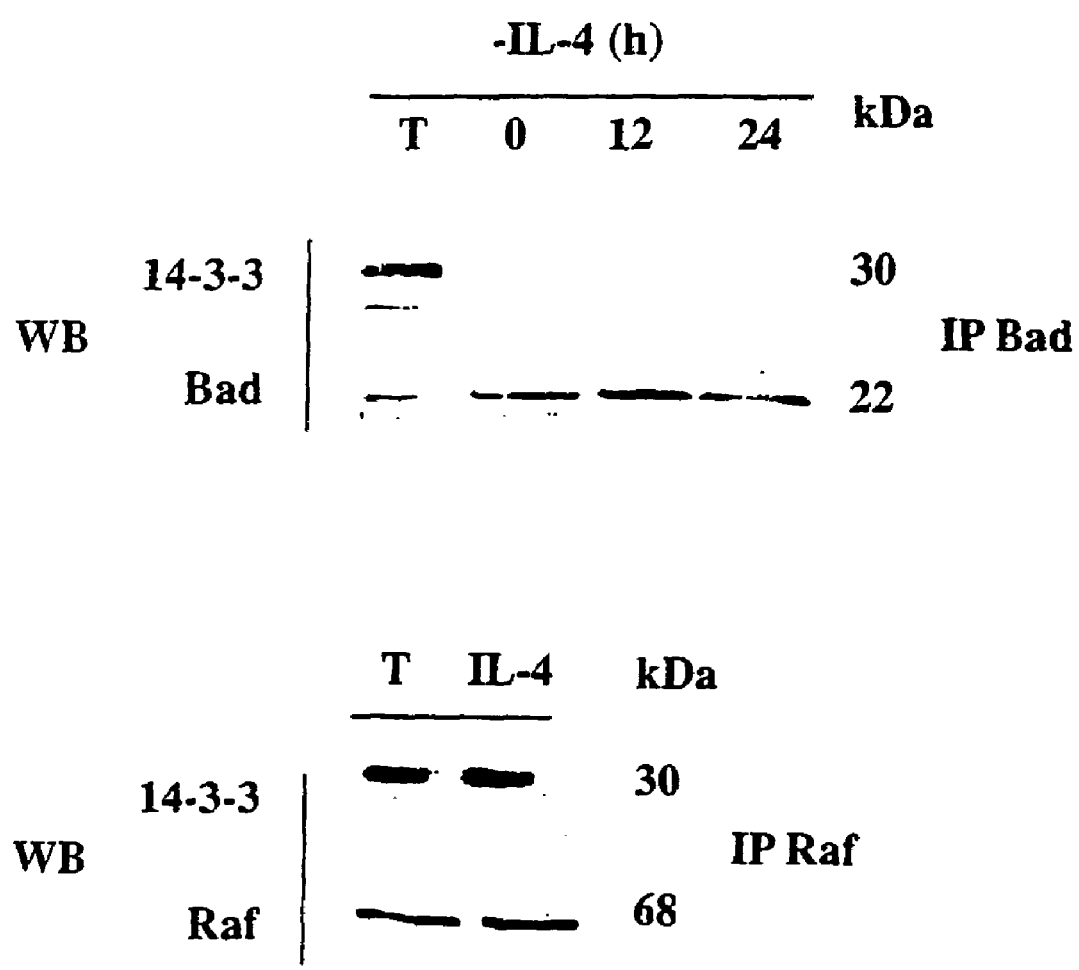

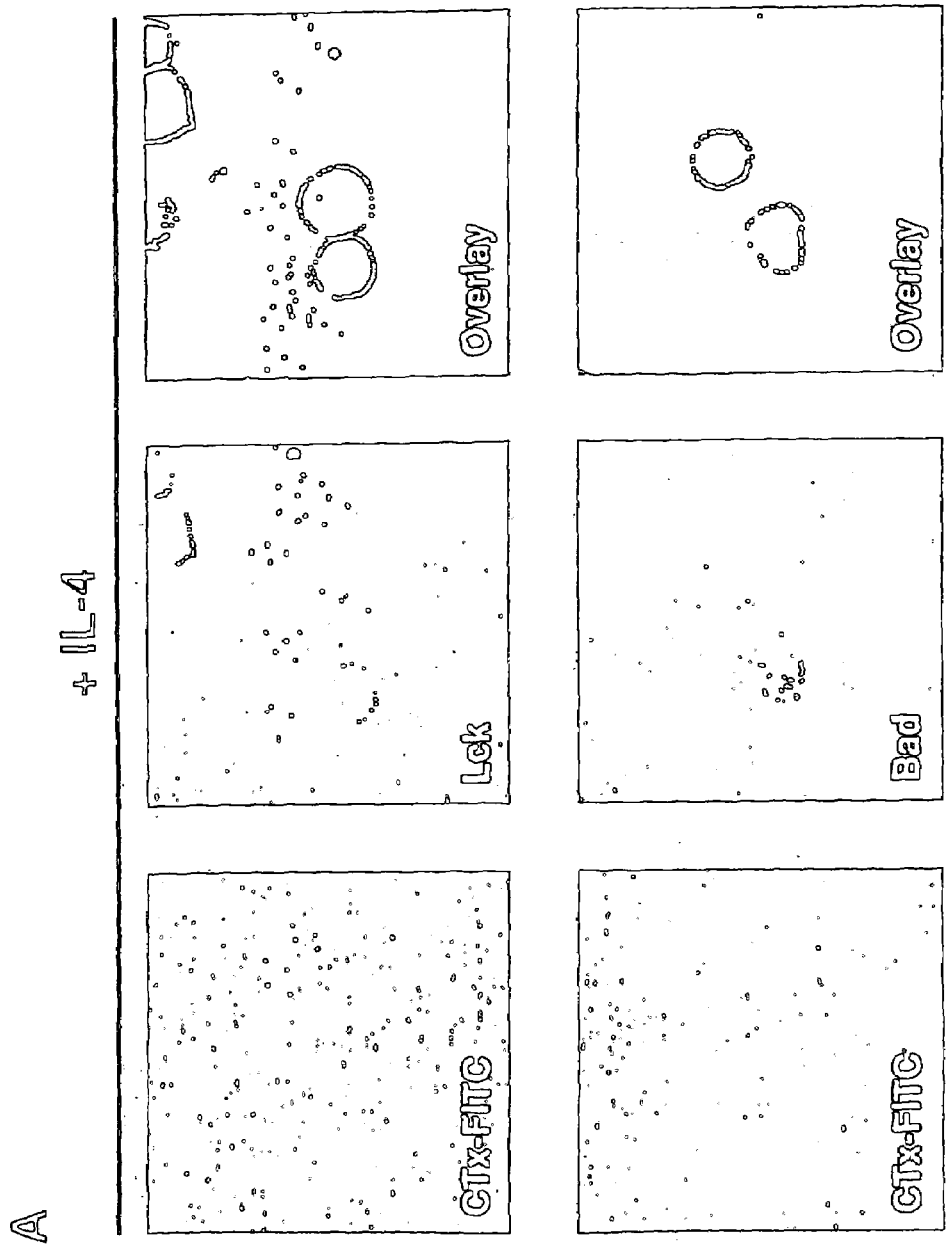
FIGURE 3A(1)

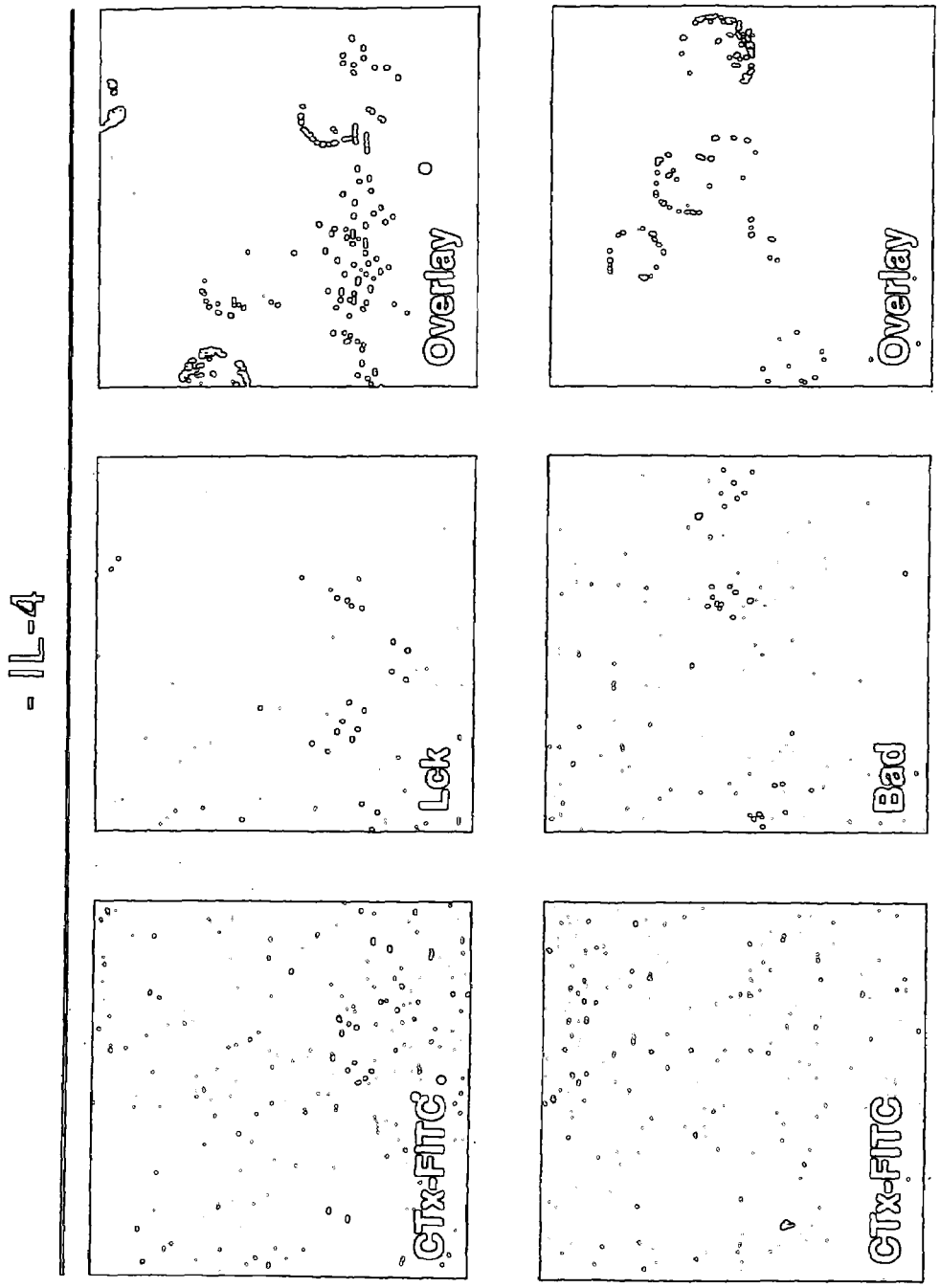
FIGURE 3A(2)

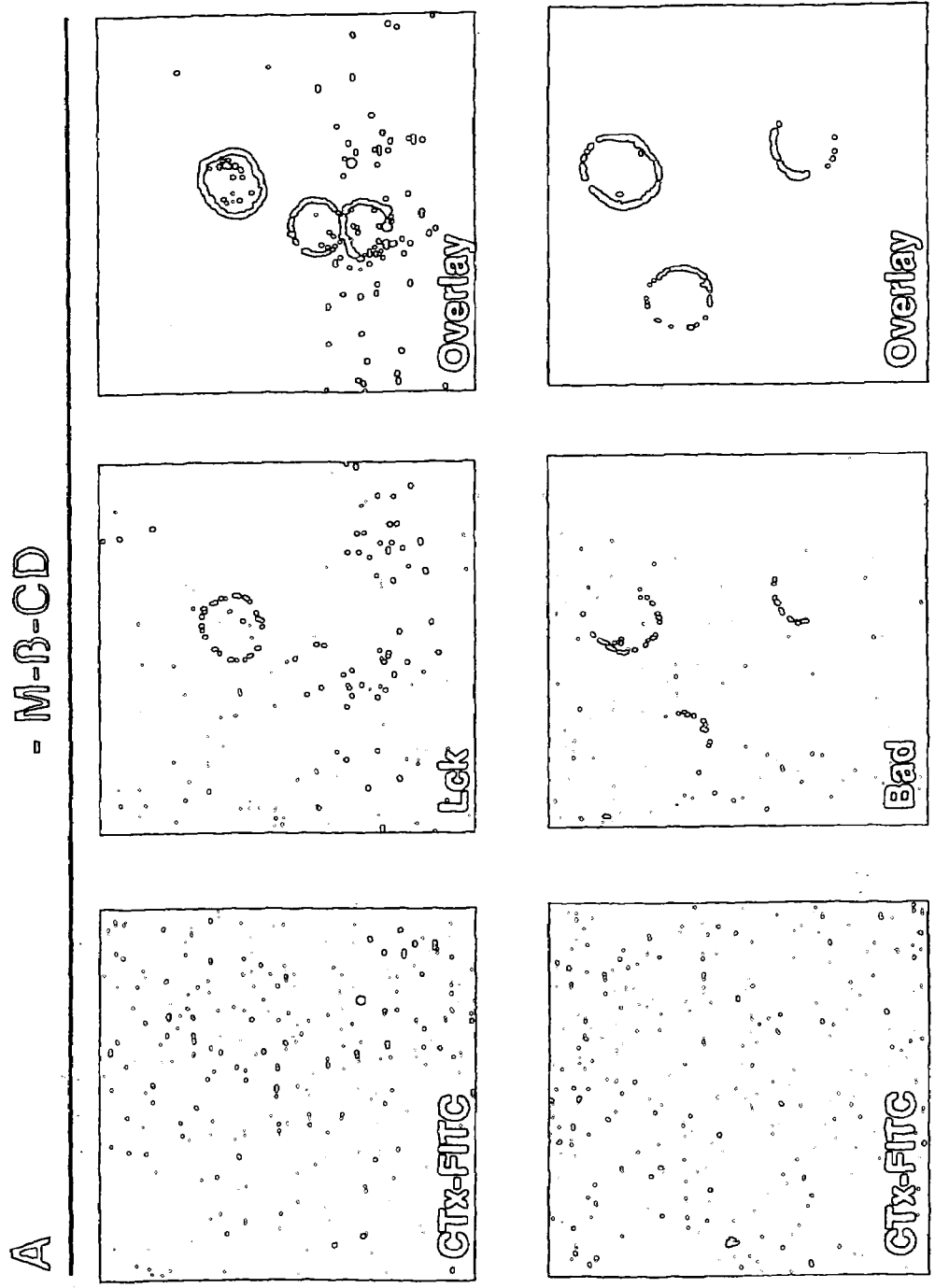
FIGURE 4A(1)

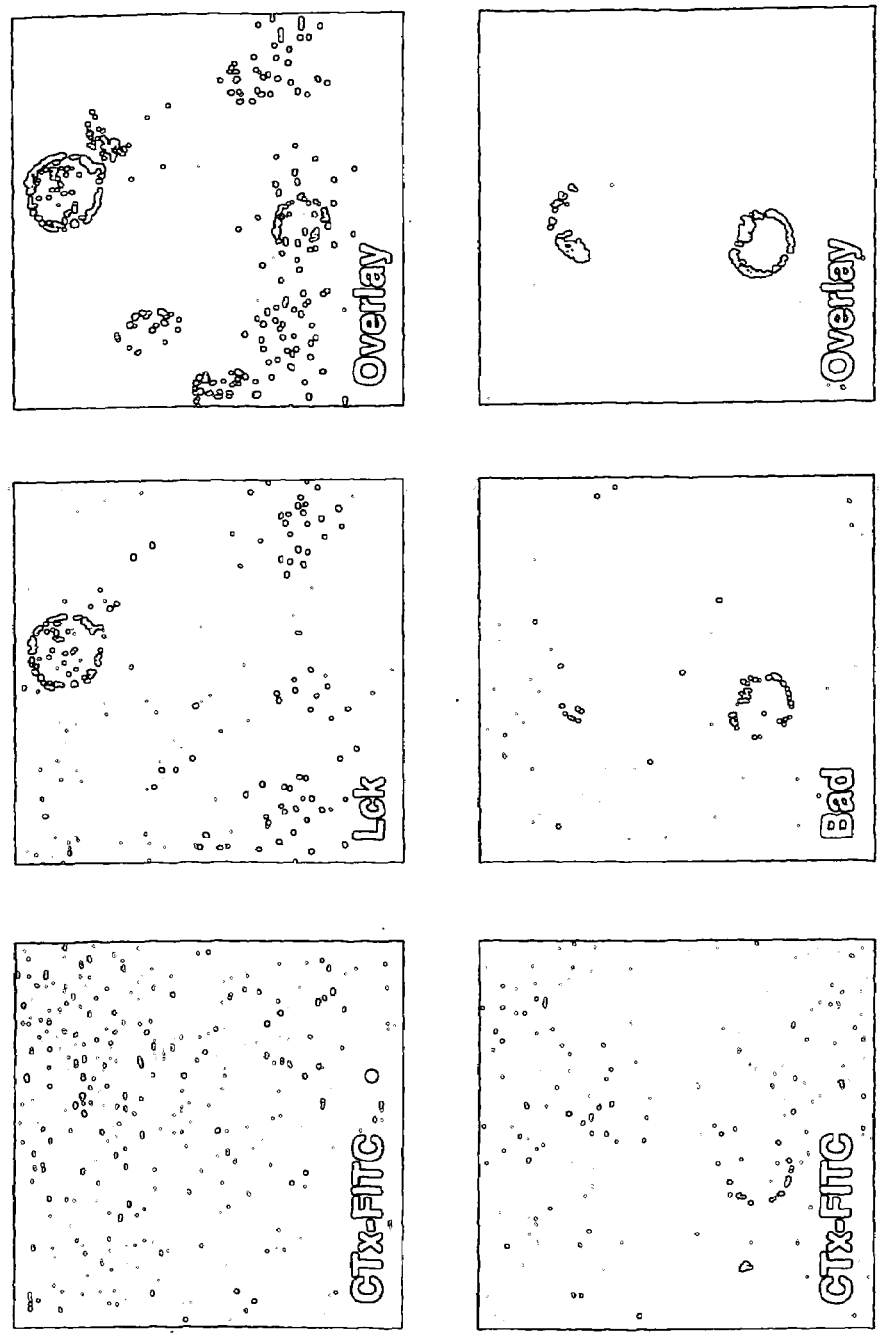
FIGURE 4A(2)

METHODS OF SCREENING APOPTOSIS MODULATING COMPOUNDS, COMPOUNDS IDENTIFIED BY SAID METHODS AND USE OF SAID COMPOUNDS AS THERAPEUTIC AGENTS

This application is a continuation of Ser. No. 10/934,513, filed Sep. 7, 2004, now abandoned, which is a continuation of International Application PCT/EP03/02921, filed Mar. 7, 2003.

The invention relates to the modulation of apoptosis in mammalian cells. More particularly, the invention provides methods for identifying novel pro-apoptotic or anti-apoptotic cellular polypeptides, methods of screening compounds which modulate apoptosis, and method of detecting early events of the apoptotic process.

Apoptosis or programmed cell death is an active process in which cells induce their self-destruction in response to specific cell death signals or in the absence of cell survival signals. This active process is actually essential in the normal development and homeostasis of multicellular organisms. It is opposed to necrosis which is cell death occurring as a result of severe injurious changes in the environment.

Apoptosis of a cell can be characterized at least by
 the rapid condensation of the cell with collapse of the nucleus but preservation of membranes; or,
 cleavage of nuclear DNA at the linker regions between nucleosomes to produce fragments which can be easily visualized by agarose gel electrophoresis as a characteristic ladder pattern.

Various pathologies occur due to a defective or aberrant regulation of apoptosis in the affected cells of an organism. For example, defects that result in a decreased level of apoptosis in a tissue as compared to the normal level required to maintain the steady-state of the tissue can promote an abnormal increase of the amount of cells in a tissue. This has been observed in various cancers, where the formation of tumors occurs because the cells are not dying at their normal rate. Some DNA viruses such Epstein-Barr virus, African swine fever virus and adenovirus, also inhibit or modulate apoptosis, thereby repressing cell death and allowing the host cell to continue reproducing the virus.

On the contrary, a defect resulting in an increase of cell death in a tissue may be associated with degenerative disorders wherein cells are dying at a higher rate than they regenerate. This is observed in various disorders, such as AIDS, senescence, and neurodegenerative diseases.

Compounds that modulate positively or negatively apoptosis can provide means for the treatment or the prevention of these disorders. As a consequence, the delineation of apoptotic pathways provides targets for the development of therapeutic agents that can be used to modulate the response of a cell to apoptotic or cell survival signals.

Progresses have been made in identifying extracellular, intracellular and cell surface molecules that regulate apoptosis. Previous studies have focused on the identification of specific cell death signals, (such as the deprivation of growth factors, the FAS/TNF system, genotoxic agents, glucocorticoïds . . . ), members of the Bcl-2 family and ICE-type proteases. But critical steps in apoptotic pathways remain to be identified.

Accordingly, there is still a need in identifying the cellular mechanisms involved in apoptotic pathways, and target for the development of therapeutic agents that can be used to modulate cell apoptosis.

Among the different transducing agents, the Bcl-2 family proteins act as an intracellular checkpoint in the apoptotic pathway. The family is divided into two functional groups (medecine/sciences 97; 13: 384–6): the proteins that suppress cell-death (anti-apoptotic members such as Bcl-2, Bcl-$X_L$, Bcl-w, Bag-1, Mcl-1, A1) and the proteins that promote cell death (pro-apoptotic members such as Bim, Nix, Hzk, Bax, Bak, Bcl-$x_S$, Bad, Bik). The Bcl-2 family has been defined by sequence homology based upon specific conserved motifs termed BCL-homology regions (BH1, BH2, BH3 and BH4 domains). BH1, BH2 and BH3 domains have been shown to be important in homodimerization or heterodimerization and in modulating apoptosis. Anti-apoptotic molecules have a specific BH4 domain.

It has been proposed that the ratio of pro-apoptotic members to anti-apoptotic members expressed in a cell determines whether this cell will respond to an apoptotic signal. Indeed., pro-apoptotic and anti-apoptotic members antagonized each other by forming inactive heterodimers (Oltvai et al., 1993, *Cell* 74: 609–619), as a consequence only the balance may promote or prevent a cell to undergo apoptosis.

More recently, it has been shown that phosphorylation of Bcl-2 proteins can also modulate their activity. Indeed, different anti-apoptotic pathways are likely to be activated by growth factors, involving phosphatidylinositol 3 kinase (PI3K), Akt kinase and Ras activated kinases. In particular, upon stimulation of cells with IL-3 and NGF, the pro-apoptotic Bad protein (Bcl-$x_L$/Bcl-2 Associated cell Death regulator, Downward, 1999, *Nature Cell Biol* 1: 33–35) becomes serine phosphorylated, resulting in association to 14-3-3 protein (Hsu et al., 1997,*Mol Endocrinol* 11: 1858 – 1867). It was proposed that such interaction facilitates the translocation of phosphorylated Bad from the mitochondrial membrane to cytosolic compartments, sequestering it therein and thus, preventing further interaction with other anti-apoptotic Bcl-2 members (U.S. Pat. No. 5,856,445). It was further shown that association of 14-3-3 protein to Bad is dependent upon serine 155 phosphorylation of Bad (WO 0110888, Apoptosis Technology Inc., 2001).

The results disclosed in the present invention indicate that some pro- or anti-apoptotic proteins especially of the Bcl-2 family, are regulated through a newly identified subcellular localization that is in lipid rafts formed in the plasma membrane. This observation offers a way to a novel general mechanism of regulation of cell apoptosis that may play a role in the regulation of pro- or anti-apoptotic molecules in response to cell death or cell survival signals.

Localization of proteins to distinct subcellular compartments, including membranes, is a critical event in multiple cellular pathways. Plasma membranes of many cell types contain microdomains commonly referred to as lipid rafts, which are biochemically distinct from bulk plasma membranes (Brown and London, 1998, *Annu Rev Cell Dev Biol* 14: 111–136). These domains consist of dynamic assemblies of sphingolipids and cholesterol. More specifically, the presence of saturated hydrocarbon chains in sphingolipids allows for cholesterol to be tightly intercalated, leading to the presence of distinct liquid-ordered phases, and thereby more fluid, lipid bilayer. Lipid rafts can be isolated by subcellular fractionation and density gradient ultracentrifugation according to methods described in Hacki et al. (*Oncogene* 2000 19: 2286–2295) and Millan et al. (*Eur J Immunol* 1998 28: 2675–3684). They can also be visualized in intact cells by confocal microscopy using, for example, fluorescently labelled cholera toxin subunit B (CTx) which binds to the ganglioside GM1 (Harder et al., 1998, *J Cell*

*Biol* 141: 929–942). One key element of lipid rafts is that they can include or exclude proteins to varying degrees.

In T cells, a number of proteins involved in signal transduction such as IcK, Lat, copurify with lipid rafts isolated on sucrose gradient. Disruption of rafts integrity by a variety of methods inhibits early activation events, supporting a critical role for these domains in the recruitment for signalling and thus, in signal transduction from cell surface receptors. For example, the antitumor ether lipid 1-O-octadecyl-2-O-methyl-rac-glycero-3-phosphocholine (ET-18-OCH3; edelfosine) was shown to trigger apoptosis via translocation of Fas to lipid rafts and subsequent Fas recruitment by lipid rafts (Gajate and Mollinedo, *Blood*, 2001, 98: 3860–3863).

The present invention results from the discovery of a novel mechanism of cellular regulation of the activity of pro- or anti-apoptotic molecules in a cell by translocation of these molecules into lipid rafts under non apoptotic conditions such as proliferative conditions or conditions where cells do not divide.

Indeed, the inventors have surprisingly found that interaction of a pro-apoptotic protein, such as the Bad protein, with rafts is an active process regulated by cytokines or growth factors. They have also shown that segregation of this molecule from rafts in cytokine or growth factor deprived-cells is involved in the induction of apoptosis and associated with raft disorganization.

The invention thus provides methods for identifying cellular polypeptides which have pro-apoptotic or anti-apoptotic activity in a particular cell type.

The invention also provides means for screening apoptosis modulating compounds which interfere with the newly identified mechanism of apoptosis regulation. Candidate compounds in this respect may either interfere by blocking, preventing or stimulating translocation of one or several pro- or anti-apoptotic polypeptides in lipid rafts under non apoptotic conditions. Candidate compounds may in addition or alternatively interfere by disrupting or reconstituting lipid rafts in a cell which normally produce pro- or anti-apoptotic polypeptides located in lipid rafts under non apoptotic conditions. According to another embodiment, candidate compounds may in addition or alternatively interfere by segregation of pro- or anti-apoptotic polypeptides from lipid rafts.

The invention also provides a compound capable of modulating association of a pro- or anti-apoptotic polypeptide with lipid rafts.

The invention also provides a compound capable of modulating transfer of a pro- or anti-apoptotic polypeptide between a lipid raft and another cellular localization.

The invention also provides for the use of compounds capable of modulating lipid rafts formation or of modulating translocation of pro- or anti-apoptotic proteins in rafts in the preparation of a medicine for the prevention and/or treatment of disorders induced by or associated with a defective regulation of cell death as well as of specific pathologies in which the death of infected or deregulated cells may be at least art of a therapy.

Among the several advantages of the present methods, it should be noted that the apoptotic or non apoptotic state of a cell can be determined according to the present methods in a relatively short period of time by analysing lipid raft organization. In particular, there is no need to quantify specific gene expression. The methods of the invention are thus particularly appropriate for routine high throughput screening of apoptosis modulating compounds.

Furthermore, the invention provides methods for detecting early events of the apoptotic process in a cell.

A first object of the invention is a method of screening cellular polypeptides for pro-apoptotic or anti-apoptotic activity in a cell of a particular cell-type, said method comprising:

a. culturing cells of said particular cell-type under non apoptotic conditions and culturing cells of said particular cell-type under apoptotic conditions; and,
   b. determining subcellular localisation of said cellular polypeptides in the cultured mammalian cells;

wherein a localization of a cellular polypeptide in lipid rafts in cells cultured under non apoptotic conditions and a segregation of said cellular polypeptide from lipid rafts in cells cultured under apoptotic conditions is indicative of the pro-apoptotic or an anti-apoptotic activity of said cellular polypeptide in said particular cell-type.

In a particular embodiment, said cultured cells are mammalian cells.

In a preferred embodiment, the cells cultured under non apoptotic conditions are cultured under proliferative conditions. According to the methods of the invention, cells are considered to be cultured "under non apoptotic conditions" when the proportion of cells undergoing apoptotic process in the cell culture is relatively stable in time and does not represent more than 10%, preferably, more than 1% of the whole cell population (depending upon the cell-type).

In a preferred embodiment, non apoptotic conditions are proliferative conditions.

On the contrary, cells are considered to be cultured "under apoptotic conditions" when the proportion of the cells undergoing apoptotic process increases dramatically in time to reach, after a certain period, especially for around 24 hours, from deprivation of growth or proliferation factor or by use of an apoptotic factor, more than 50% of the whole cell population.

Cells which have undergone apoptotic process can be characterized, for example, by specific cleavage of nuclear DNA which can be visualized on agarose gel electrophoresis.

As used herein, the term "cellular polypeptide" refers to any polypeptide which is produced in a cell by gene expression. It can be a polypeptide naturally encoded in said cell especially by a native gene, or a polypeptide not naturally encoded in said cell, meaning that the gene encoding said polypeptide or a coding sequence derived from said identified gene has been recombined in the genome of the cell to obtain expression. It can be a mutated form of a naturally occurring polypeptide and more specifically, a mutated form wherein the mutation is involved in abnormal subcellular localisation of said polypeptide under proliferative growth conditions.

As used herein, the term "lipid rafts" refers to dynamic-assemblies of sphingolipids and cholesterol in plasma membranes forming microdomains with distinct liquid-ordered phases, said microdomains stably retaining specific structures, such as gangliosides or polypeptides such as Lck. Lipid rafts can be biochemically isolated by subcellular fractionation and density gradient ultracentrifugation according to the methods described in Hacki et al. (*Oncogene* 2000 19: 2286–2295) and Millan et al. (*Eur J Immunol* 1998 28: 2675–3684) and in the examples below. They can also be visualized in intact cells by confocal microscopy using, for example, fluorescently labelled cholera toxin subunit B (CTx) which binds to the ganglioside GM1 which accumulate in lipid rafts (Harder et al., 1998, *J Cell Biol* 141:

929-942). More specifically, subcellular localization of a particular polypeptide in lipid rafts is determined by double immunofluorescence using a labelled marker detecting lipid rafts and another labelled marker detecting the polypeptide to localize. It can also be determined by analysing the presence of said polypeptide in subcellular fractions containing lipid rafts.

In a particular embodiment, the method of the invention is appropriate to screen a polypeptide, whose structure is known but whose function is unknown, for a pro- or anti-apoptotic activity in a particular cell type. In particular, the one skilled in the Art can use the method of the invention to screen polypaptides which are suspected to be involved in apoptosis regulation according to specific features such as specific structural domains. The screening of cellular polypeptides is however not necessarily limited to cellular polypeptides of known structure.

Several pro-apoptotic proteins have been identified so far, however, expression pattern of these proteins may vary depending upon the cell type. The method of screening is thus also useful in determining whether a putative cellular polypeptide, known to be pro- or anti-apoptotic in a certain cell-type is involved in apoptosis modulation in another cell-type.

In a particular embodiment, the screened polypeptides belong to the Bcl-2 family. As mentioned hereabove, the Bcl-2 family members are characterized by sequence homology based upon specific conserved motifs termed BCL-homology regions (BH1, BH2, BH3 and BH4 domains). Accordingly, their subcellular localisation can be determined by the use of a molecule which specifically recognizes a BH domain. Such molecules encompass for example monoclonal antibodies or polyclonal antibodies specifically recognizing a BH domain. One example of a molecule that interacts with BH3 motif in PP1a (Ayllon, et al. 2000. EMBO J.; 19: 2237–2246). Examples of molecules that interact with BH4 motif are review in Admas, J. M. and Cory, S. (1998) Science, 281, 1322). In a particular embodiment, a molecule which specifically recognizes a BH4 domain is used to screen preferably for anti-apoptotic molecules. In another particular embodiment, a molecule which specifically recognizes a BH3 domain is used to screen for pro- or anti-apoptotic molecules. A combination of molecules recognizing the different BH domains can also be used, for example to screen for pro-apoptotic molecules which have only the BH3 domain.

The method of the invention is also appropriate to screen novel polypeptides of the Bcl-2 family whose structure and function are unknown at least in part, but which can be easily isolated using molecular recognition of their BH domain(s). As a result, in a preferred embodiment, said screened cellular polypeptides are first isolated from biochemically isolated lipid rafts of said mammalian cells cultured in proliferative conditions by the use of a molecule which specifically recognizes a BH domain. More specifically, the polypeptides present in the isolated lipid rafts can be separated on a gel and analysed by Western Blot analysis using an antibody which recognizes a BH domain or by similar methods of protein analysis. The polypeptides recognized by a BH domain can be isolated and antibodies which recognize each isolated polypeptides can be produced according to usual methods well known in the art. The subcellular localization of one or more of the isolated polypeptides is then determined according to the method of the invention using such specific antibodies to screen for apoptotic activity.

The proteins which are associated with lipid rafts may have a transmembrane domains or have undergone post-translational modifications such as myristoylation. In another specific embodiment, said screened cellular polypeptides are further isolated by the use of a molecule which specifically recognizes a mirystoylated polypeptide.

In a preferred embodiment, the method is carried out for screening cellular polypeptides of a cell type characterized by the production of Bad protein, i.e. Bad$^+$ cell type. According to another preferred embodiment, the cells are characteristic of the immune system, and most preferably are T cell lines.

Indeed, it is shown, in the examples below, that the pro-apoptotic Bad protein is sequestered in lipid rafts of IL-4 stimulated T-cells and segregates from rafts in IL-4 deprived T-cells.

More specifically, it is shown in the Example that Bad can be co-purified with lipid-rafts by subcellular fractionation and density gradient ultracentrifugation from cells under non-apoptotic conditions, especially under proliferative conditions. These results indicate that Bad is strongly associated with lipid rafts in cells cultured under non apoptotic conditions such as proliferative conditions.

Cellular polypeptides which physically interacts with Bad protein in isolated lipid rafts of Bad$^+$ cells thus constitute preferred putative polypeptides to screen for pro- or anti-apoptotic activity. Accordingly, in a preferred embodiment, the screened cellular polypeptides are isolated from isolated lipid rafts of Bad$^+$ cells cultured under proliferative conditions and are selected among the polypeptides which interact physically with the Bad protein.

Naturally, the invention also pertains to the newly identified cellular polypeptides having pro- or anti-apoptotic activity and their use in providing means for modulating apoptosis in cells, such as mammalian cells, expressing these polypeptides.

It is another object of the invention to provide a method of screening compounds for their capacity to modulate apoptosis in cells, which produce pro- or anti-apoptotic polypeptides which are located in lipid rafts when said cells are cultured under non apoptotic conditions, said method comprising:
  a) culturing said cells in a growth medium maintaining non apoptotic conditions;
  b) contacting said cultured cells with a candidate compound;
  c) determining the level of one or several pro- or anti-apoptotic polypeptides associated to lipid rafts;
  d) selecting the compound which interferes with the association of one or several pro- or anti-apoptotic polypeptides with lipid rafts, said compound having the capacity to modulate apoptosis.

A compound interferes with the association of a pro- or anti-apoptotic polypeptide when it modifies said association, including when it alters the chemical and/or the physical nature of said association or when it provides or influences segregation of pro- or anti-apoptotic polypeptides from lipid rafts, or when it prevents said association, or also when it acts on and especially promotes disruption of lipid rafts or more generally alter constitution of lipid rafts.

The invention further relates to a method of screening compounds for their capacity to promote apoptosis in cells, said method comprising
  a) culturing cells in a growth medium maintaining non apoptotic conditions; wherein said cells produce a pro-apoptotic protein which is located in lipid rafts under non apoptotic conditions of said cells;
  b) contacting said cultured cells with a candidate compound; and, c) determining the absence or the presence of lipid rafts in said cultured cells;

d) in case of presence of lipid rafts, optionally determining the level of pro-apoptotic protein located in the lipid rafts, wherein the absence of lipid rafts in the plasma membrane of cells incubated with said candidate compound or if determined, the reduced level of pro-apoptotic protein in the rafts is indicative that said compound promotes apoptosis.

The invention also relates to a method of screening compounds for their capacity to inhibit or prevent apoptosis of cells, said method comprising:

a) culturing cells in a growth medium for maintaining non-apoptotic conditions; wherein said cells produce a pro-apoptotic protein which is located in lipid rafts under non apoptotic conditions;

b) contacting said cells with a candidate compound;

c) culturing cells under apoptotic conditions; and, d) determining the absence or the presence of lipid rafts;

e) in the case of presence of lipid rafts, optionally determining the level of pro-apoptotic protein located in the lipid rafts, wherein the presence of lipid rafts in the plasma membranes of cells incubated with said candidate compound and optionally the maintained level of proapoptotic protein in the rafts is indicative that said candidate compound inhibits or prevents apoptosis.

In a preferred embodiment, the cells are cultured in a growth medium comprising at least a cytokine or a growth factor necessary for maintaining proliferative growth conditions and step c) of the method comprises depriving the cells of said cytokine or growth factor necessary for maintaining proliferative growth conditions.

As used herein, the term "compound" refers to inorganic or organic chemical or biological compounds either natural (isolated) or synthetic, and especially encompass nucleic acids, proteins, polypeptides, peptides, glycopeptides, lipids, lipoproteins and carbohydrates.

Any cells in which pro- or anti-apoptotic proteins may be translocated in lipid rafts can be used in the methods of the invention. In a preferred embodiment of the methods of the invention, cells are mammalian cells.

Mammalian cells which are used in the methods of screening compounds can be any mammalian cells whose cell survival can be controlled by a specific cytokine or growth factor. In preferred embodiments of the above methods, the cultured mammalian cells are selected among those which produce the Bad protein as a pro-apoptotic protein. More specifically, preferred mammalian cells which produce a Bad protein are selected among cells characteristic of the immune system, and more preferably among T cells.

As used herein, the term "cytokine or growth factor" refers to any molecule which is necessary to be present in a growth medium to prevent apoptotic process of a cultured cell and/or to promote cell proliferation. Known cytokines include any interleukin. Known growth factors include the fibroblast growth factors, bFGF, aFGF, FGF6, the hepatocyte growth factors HGF/SF, the epidermis growth factor, EGF and other characterized growth factors such as IGF-1, PDGF, LIF, VEGF, SCF, TGFb, TNFa, NGF, BMP, neuregulin, thrombopoïetin and growth hormone. Growth factors according to the invention can include also, progestagenes and derivatives thereof (progesterone), oestrogens and derivative thereof (oestradiol), androgenes (testosterone), mineralocorticoïds and derivatives thereof (aldosterone), LH, LH-RH, FSH et TSH hormones, T3, T4, and retinoidic acid, calcitoniine E2 and F2/alpha prostaglandins. Glucocorticoïids (natural or hemisynthetic, i.e. hydrocortisone, dexamethasone, prednisolone or triamcinolone), can also be used.

Cells characteristic of the immune system can be advantageously cultured under stimulation with an interleukin for maintaining proliferative growth conditions. In particular, IL-4, IL-2 or IL-9 interleukin can be used in this context, or a mixture thereof.

However, any available apoptosis model can be used to select the cell type and the factors for non apoptotic conditions such as the growth factor or cytokine, used in the methods. As used herein, the term "apoptosis model" comprises any teaching providing a way to control cell apoptosis in a cell culture of a specific cell type by the use of specific factors for non apoptotic conditions such as a specific cytokine or growth factor or a mixture thereof. Such apoptosis models are for example the control of IL-4 stimulated T-cell lines, IL3 and hematopoietic progenitor, PC12 and CRH (corticotropin-releasing hormone), HN9.10.

A candidate compound may modulate apoptosis by blocking or preventing the association of said pro- or anti-apoptotic polypeptide with lipid rafts. In this context, the subcellular localisation of said pro- or anti-apoptotic polypeptide in lipid rafts is no more observed in cells incubated with the compound when compared to cells not incubated with the compound, or, at least, lipid rafts subcellular localisation of said pro- or anti-apoptotic polypeptide is significantly reduced when compared to cells not incubated with the compound.

It is another object of the invention to provide compounds capable of modulating association of a pro- or anti-apoptotic polypeptide with lipid rafts.

Some of these compounds may modulate apoptosis by preventing the association of a pro- or anti-apoptotic polypeptide with lipid rafts, by promoting segregation of a pro- or anti-apoptotic polypeptide from lipid rafts or by promoting disruption of lipid rafts.

Some of these compounds may modulate apoptosis by preventing the segregation of a pro- or anti-apoptotic polypeptide from lipid rafts, by promoting the association of a pro- or anti-apoptotic polypeptide with lipid rafts or by promoting constitution of lipid rafts.

It is another object of the invention to provide compounds capable of modulating transfer of a pro- or anti-apoptotic polypeptide between a lipid raft and another cellular localization.

Some of these compounds may modulate apoptosis by preventing transfer of a pro- or anti-apoptotic polypeptide from a cellular localization, other than a lipid raft, to a lipid raft or from a lipid raft to another cellular localization.

Some of these compounds may modulate apoptosis by promoting transfer of a pro- or anti-apoptotic polypeptide from a cellular localization, other that a lipid raft, to a lipid raft or from a lipid raft to another cellular localization.

In a preferred embodiment, the compounds of the invention modulating apoptosis are capable of modulating the association of a pro-apoptotic protein of Bcl-2 family, especially Bad, with lipid rafts or transfer of said protein between lipid rafts and another cellular localization.

Some of said compounds may promote apoptosis in a Bad-producing cell by preventing association of Bad with lipid rafts, by promoting segregation of Bad from lipid rafts or by promoting disruption of lipid rafts.

Some of said compounds may inhibit apoptosis in a Bad-producing cell by promoting association of Bad with lipid rafts, by preventing segregation of Bad from lipid rafts or by promoting constitution of lipid rafts.

In a particular embodiment, a compound of the invention may inhibit apoptosis of a Bad-producing cell by preventing transfer of Bad to mitochondria after Bad segregation from lipid rafts. Such a compound may interact with Bad by means of a motif similar to the lipid raft motifs which allow association of Bad to lipid rafts.

Lipid rafts subcellular localisation of said pro or anti-apoptotic polypeptide can be quantified by any quantitative analysis methods available in the art. A significant reduction of lipid rafts subcellular localisation is observed when the level of pro- or anti-apoptotic polypeptide is reduced to at least 50%, preferably 90% in cells incubated with the candidate compound or compared to cells not incubated with the candidate compound.

A candidate compound may modulate apoptosis by blocking or preventing the segregation of said pro- or anti-apoptotic polypeptide from lipid rafts. In this context, the subcellular localisation of said pro- or anti-apoptotic polypeptide in lipid rafts of cells cultured under conditions promoting pro- or anti-apoptotic protein segregation (e.g., apoptotic conditions for pro-apoptotic proteins) remains observed in cells incubated with the compound when compared to cells not incubated with the compound and lipid rafts subcellular localisation of said pro- or anti-apoptotic polypeptide is significantly maintained when compared to cells not incubated with the compound.

Lipid rafts subcellular localisation of said pro- or anti-apoptotic polypeptide can be quantified by any quantitative analysis methods available in the art. A significant maintenance is observed when the level of pro- or anti-apoptotic polypeptide is maintained to at least 50%, preferably 90% in cells incubated with the candidate compound or compared to cells not incubated with the candidate compound or compared to cells not incubated with the candidate compound.

By "determining the absence of lipid rafts", it is understood that lipid rafts in cells incubated with the candidate compound are not detected, or at least, are detected as traces, or are detected in a significantly reduced level (i.e., minimum 20% less) with the methods disclosed in the present invention as compared with a culture of cells not incubated with the candidate compound as a control. The proportion of lipid rafts in a cell can be compared between the cell cultures using any quantitative analysis methods available in the art. A significant reduction of lipid rafts is observed when their proportion is reduced from 20%, preferably is reduced to at least 50%, preferably 90% in cells incubated with the candidate compound to the control. For example, by confocal microscopy analysis, the profile of fluorescence can be quantified by image analysis of cells incubated with the candidate compound and cells not incubated with the candidate compound.

Similarly, by "determining the presence of lipid rafts", it is understood that lipid rafts in cells incubated with the candidate compound are detected in substantially the same amount as compared with a culture of cells not incubated with the candidate compound as a control.

Methods to isolate lipid rafts have been described below. More specifically, it is possible to isolate lipid rafts from mammalian cells, by cell fractionating over sucrose gradient and immunoblotting subcellular fractions with markers specific for rafts in order to identify rafts containing subcellular fractions. The presence or the absence of lipid rafts can be thus determined in a specific embodiment by the following steps i) recovering the cultured cells incubated with said compound and resuspending said cells in a buffer appropriate for subcellular fractionation, such as gradient sucrose buffer;
ii) ultracentrifugating the fractionated cells;
iii) recovering the subcellular fraction which should contain lipid rafts; and,
iv) determining whether the recovered subcellular fraction contains ganglioside and/or lipid raft associated molecule(s).

As used herein, "the subcellular fraction which should contain lipid rafts" is the subcellular fraction corresponding to the banded organelles of the gradient which contains lipid rafts in a gradient obtained with cells cultured under non apoptotic conditions. Naturally, in apoptotic conditions, the corresponding cell fraction will contain much less lipid rafts.

Lipid rafts and lipid rafts subcellular localisation of pro- or anti-apoptotic polypeptides can also be directly visualized in intact cells by confocal microscopy using a molecular marker which specifically binds to a raft-associated molecule or a ganglioside.

Such preferred molecular markers are, for example, the cholera toxin subunit B (CTx) which specifically recognizes ganglioside GM1, anti-Bad antibody or anti-Lck antibody. More generally, any antibody directed to any cellular polypeptide newly identified according to the method of the invention as described above can be used as a molecular marker specific for raft.

The invention also concerns the compounds identified by the methods of screening.

Such compounds identified by the above methods of the invention are useful for the prevention and/or treatment of disorders induced by or associated with a defective regulation of cell death or of specific pathologies where death of infected or deregulated cells may be at least part of a therapy.

The invention further provides a use of a compound capable of modulating lipid rafts formation, in the preparation of a medicine for the treatment of disorders induced by or associated with a defective regulation of cell death.

In a preferred embodiment, said defective regulation affects cells which produce Bad protein, more preferably, cells of the immune system and most preferably T-cells.

When said defective regulation of cell death results in an abnormal decrease of cell death, the used compound is preferably a compound which is capable of disrupting lipid rafts, thereby promoting apoptosis. Such compounds are for example, methyl-β-cyclodextrin or filipin. Examples of disorders resulting in an abnormal decrease of cell death are cancer diseases and especially lymphoproliferative cancers, infectious diseases and especially viral diseases, inflammatory diseases or auto-immune diseases.

Conversely, when defective regulation of apoptosis results in an abnormal increase of cell death, the used compound is preferably a compound capable of reconstituting lipid rafts in the plasma membrane of cells, such as edelfosine thereby preventing apoptosis. Examples of disorders resulting in an abnormal increase of cell death is diseases associated to senescence, neuro-degenerative diseases, including Alzheimer disease, ischemic cell death, wound-healing or AIDS.

The invention provides new means to detect early events of the apoptotic process. In particular, the invention enables to identify the apoptotic state of a cell by determining the presence or the absence of lipid rafts. Accordingly, another object of the invention is an in vitro method for the detection of a defective regulation of apoptosis, in a sample of cells of an individual, said method comprising determining the presence or the absence of lipid rafts in said cells, wherein the absence of said lipid rafts is indicative of a defective regulation of apoptosis.

Examples of methods for determining the presence or absence of lipid rafts in cells have already been described above. In a preferred embodiment, the presence or the absence of lipid rafts is determined by detecting the presence or absence of a pro-apoptotic or an anti-apoptotic protein which is known to be located in lipid rafts under proliferative growth conditions, such as the Bad protein, or any other protein, and especially a cellular polypeptide identified according to the method of the invention exposed above.

In a specific embodiment, said isolated cells are cells characteristic of the immune system of an individual affected by a lymphoproliferative disease.

Naturally, the invention also concerns a use of a compound appropriate for detecting the presence of lipid rafts, in the in vitro detection method described above.

Examples of a compound appropriate for detecting the presence of lipid rafts is a compound which specifically recognizes Bad protein, Lck protein or ganglioside GM1. In a specific embodiment, said compound used in the in vitro detection method is selected among cholera toxin subunit B (CTx), anti-Bad antibody and anti-Lck antibody.

LEGENDS TO THE FIGURES

FIG. 1. Effect of IL-4 on association of Bad to 14-3-3 protein

Cytoplasmic extracts from $10 \times 10^6$ IL-4-stimulated or -deprived cells were immunoprecipitated with anti-Bad or anti-Raf antibodies and blotted with anti-14-3-3, anti-Raf and anti-Bad. Total extracts (lane T) were used as a positive control of 14-3-3 and Raft expression. Similar results were obtained in three independent experiments.

FIG. 2. Subcellular localization of Bad in IL-4-stimulated or -deprived cells.

A) Anti-Bad, anti-Lck (rafts), CTx-Biotin (GM1 ganglioside, rafts), anti-caspase 3 (cytosol), anti-calnexin (endoplasmic reticulum, ER) and anti-cytochrome C (mitochondria) immunoblot analysis of subcellular fractions from IL-4-stimulated or -deprived cells. The fractions (1 to 4) were prepared by sucrose gradient ultracentrifugation and tested for their purity using antibodies against mitochondria, rafts, ER and cytosol. Nuclear fraction is not shown in the blot (fraction 5). Protein loaded per well in each gradient fraction corresponds to that of $5 \times 10^6$ cells. Total extracts, 30 μg of protein. Similar results were obtained in three independent experiments. B) IL-4-stimulated or -deprived cells were Triton X-100 extracted and fractionated in Optiprep flotation gradient. Fractions were collected from the top to the bottom of gradient and analyzed by western blot. Only the first, insoluble proteins (I) and the last fraction, soluble proteins (S) are shown. Similar results were obtained in two independent experiments.

FIG. 3. Rafts localization of Bad in IL-4-stimulated cells

A) IL-4-stimulated or -deprived cells were stained with CTx-FITC and either anti-Lck or anti-Bad antibodies as indicated, followed by Cy3-labeled secondary antibody and analyzed by confocal microscopy.

Similar results were obtained in three independent experiments. Single confocal sections show fluorescence in green (FITC) and red (Cy3). B) IL-4-stimulated or -deprived cells were stained with anti-Bad and anti-mitochondria antibodies, followed by FITC- and Cy3-labeled secondary antibodies and analyzed as above. Similar results were obtained in three independent experiments.

FIG. 4. Methyl-β-cyclodextrin (M-β-CD) treatment abolishes association of Bad to rafts and induces apoptosis.

A) IL-4-stimulated cells were serum-starved for 30 min and then treated with or without 10 mM M-β-CD for 30 min at 37° C. before incubation with CTx-FITC and anti-Bad or anti-Lck antibodies, followed by Cy3-labeled secondary antibody. Then, cells were analyzed by confocal microscopy. Similar results were obtained in two independent experiments. Single confocal sections show green (FITC) and red (Cy3) fluorescence. B) IL-4-stimulated cells were serum-starved for 30 min and then treated with or without 10 mM M-β-CD for 30 min at 37° C., then washed and transferred to complete medium supplemented with IL-4. At different times, apoptosis was measured. Sub G1 region of the fluorescence scale was used to determine the percentage of cells present in the initial step of apoptosis. Similar results were obtained in two independent experiments. White bars, control cells; grey bars, M-β-CD-treated cells.

Figure 5:
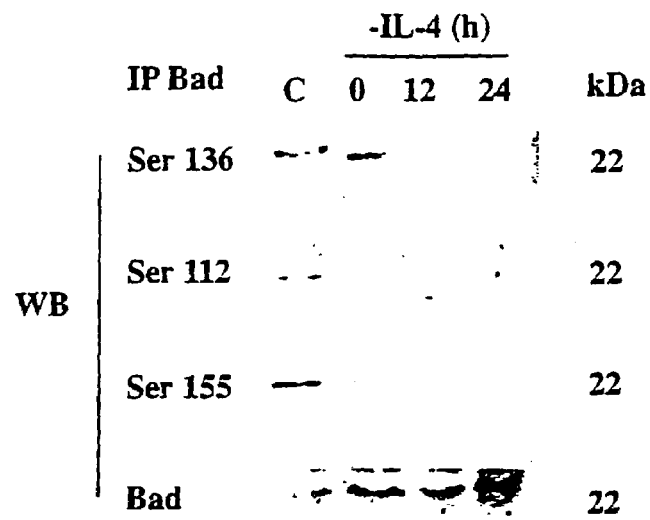
Figure 5:
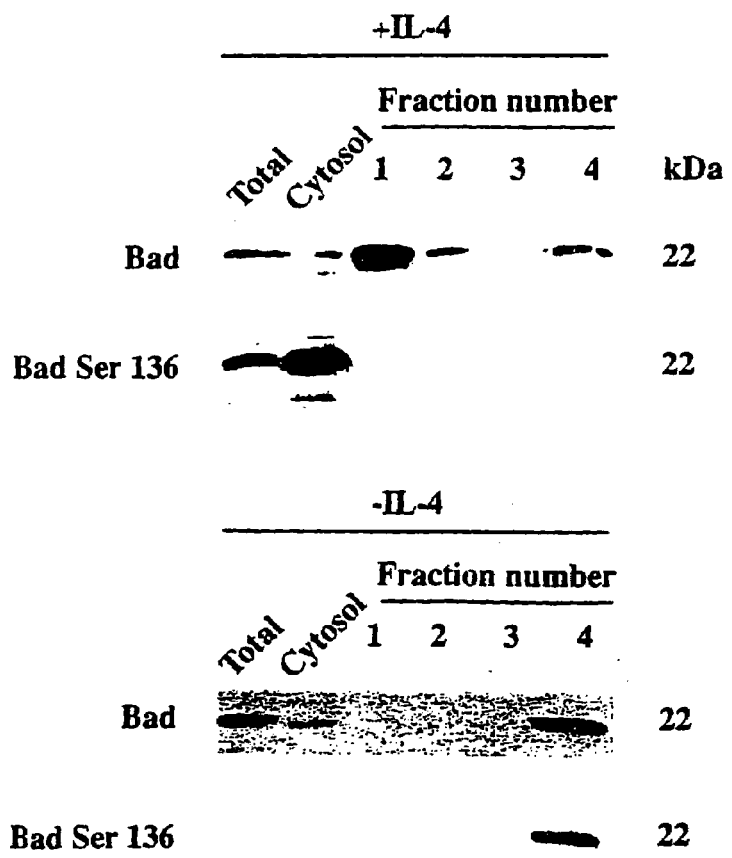

FIG. 5. Effect of IL-4 on serine phosphorylation of Bad.

A) Cytoplasmic extracts from IL-4-stimulated or -deprived cells were immunoprecipitated with anti-Bad antibody and blotted with anti-Bad serine 136, 112 and 155. As internal control, the blot was developed with anti-Bad. Positive control for serine 112 and 136 phosphorylation, IL-2-stimulated cells; positive control for serine 155 phosphorylation of Bad, Bad-transfected COS cells (C). B) Western blot from FIG. 2A was proved with anti-Bad serine 136 antibody. Molecular weight of the corresponding proteins is shown.

EXAMPLES

1. Materials and Methods 1.1 Cells, Lymphokines and Reagents

TS1αβ is a murine T cell line that can be propagated independently in IL-2, IL-4 or IL-9 Cells were cultured in RPMI-1640 as previously described (Pitton et al., 1993, Cytokine 5, 362–371). Murine rIL-4 or supernatant of a HeLa subline transfected with PKCRIL-4.neo was used as a source of murine IL-4. Fluorescein isothiocyanate (FITC-)-labeled cholera toxin (CTx) B subunit, CTx-Biotin and methyl-β-cyclodextrin (M-β-CD) were obtained from Sigma-Aldrich (St. Louis, Mo.). Cy3- and Cy2-conjugated secondary antibodies were purchased from Molecular Probes (Eugene, Oreg.). Anti-mitochondria serum (mito 2813, pyruvate dehydrogenase) was a gift from Dr A. Serrano (CNB, Madrid, Spain).

1.2 Immunoprecipitation and Western Blot

Cells ($1 \times 10^7$) were IL-4-stimulated or -deprived and lysed for 20 min at 4° C. in lysis buffer (50 mM Tris-HCl pH 8, 1% Nonidet P-40, 137 mM NaCl, 1 mM $MgCl_2$, 1 mM $CaCl_2$, 10% glycerol and protease inhibitor mixture). Lysates were immunoprecipitated with the corresponding antibody (Calbiochem Transduction Laboratory). Protein A-Sepharose was added for 1 h at 4° C. and, after washing, immunoprecipitates were separated by SDS-PAGE. Alternatively, cells were lysed in Laemmli sample buffer and protein extracts separated by SDS-PAGE, transferred to nitrocellulose, blocked with 5% non fat dry milk in Tris-buffered saline (TBS, 20 mM Tris HCl pH 7.5, 150 mM NaCl) and incubated with primary antibody in TBS/0.5% non fat dry milk. Membranes were washed with 0.05% Tween 20 in TBS and incubated with PO-conjugated secondary antibody. After washing, proteins were developed using the ECL system.

1.3 Cell Cycle Analysis

A total of $2\times10^5$ IL-4-stimulated cells treated with or without M-β-CD were washed, resuspended in PBS, permeabilized with 0.1% Nonidet P-40 and stained with 50 µg/ml propidium iodide (PI). At different times, samples were analyzed using a EpicsXL flow cytometer (Coulter, Hialeah, Fla.). Apoptosis was measured as the percentage of cells in the sub-$G_1$ region of the fluorescence scale having an hypodiploid DNA content.

Cell cycle was also analyzed by annexin staining. A total of $2\times10^3$ cells were washed with ice-cold PBS diluted in ice-cold binding buffer and stained with annexin and propidium iodide. Samples were maintained on ice for 10 min in the dark and then analyzed by flow cytometry.

1.4 Subcellular Fractionation

Subcellular fractionation was performed as previously described (Hacki et al, 2000, Oncogene 19, 2286–2295; Millan and Alonso, 1998, Eur. J. Immunol. 28, 3675–3684). Briefly, IL-4-stimulated or -deprived cells were washed in PBS and then resuspended for 2 min in extraction buffer STE (10 mM Hepes pH 7.4, 1 mM EDTA, 0.25 mM sucrose, 2 µg/ml aprotinin, 10 µg/ml leupeptin, 1 mM PMSF, 1 µg/ml pepstatin). The extract was inspected under the microscope and more than 95% of the cells were lysed. The homogenates were applied to a linear gradient sucrose (0.73 to 1.9M) and ultracentrifuged at 20,000 g overnight. The banded organelles were recovered by syringe, diluted with an equal volume of 10 mM Hepes buffer and sedimented at the speed appropriated for the respective organelles. The purity of the organelles was determined by Western blot using antibodies against specific markers: anti-cytochrome C for mitochondria, anti-Lck and CTx-Biotin for rafts, anti-calnexin for endoplasmic reticulum (ER) and anti-caspase 3 for cytosol. For preparation of cytosol, the homogenate was precentrifuged at 750 g for 10 min to remove nuclei and unbroken cells, followed by a centrifugation a 100,000 g for 1 h to clear off the membranes.

1.5 CTx-FITC Labeling

IL-4-stimulated or -deprived cells were fixed with 1% paraformaidehyde for 5 min on ice, permeabilized and then incubated with CTx-FITC (20 min, 6 µg/ml) and anti-Bad antibody for 1 h in PBS-BSA. Cy3-labeled secondary antibody was added and incubated for 1 h. Finally, and after several washing steps, cells were incubated with methanol at $-20°$ C. for 10 min, mounted wiht Vectashield medium, and analyzed by confocal microscopy. The program used for quantification of samples was Leica TSC NT version 1.5.451 (Leica, Lasertechnik, Heidelberg, Germany).

1.6 Cholesterol Depletion

IL-4-stimulated serum-deprived cells were treated for 30 min at $37°$ C. with 10 mM M-β-CD, washed and then incubated with CTx-FITC. and anti-Bad or anti-Lck antibodies as above. Secondary antibody was added and incubated for 1 h. Finally, cells were incubated with methanol at $-20°$ C. for 10 min and mounted as described above.

1.7 Triton X-100 flotation

IL-4-stimulated or -deprived cells were lysed in TXNE buffer (50 mM Tris HCl pH 7.4, 150 mM NaCl, 5 mM EDTA, 0.2% Triton X-100) containing protease inhibitor mixture. Detergent insoluble membranes were isolated by ultracentrifugation (17,000 g, 4 h, $4°$ C.) in 30–35% gradient of Optiprep as previously described (Mañes et al., 1999, EMBO J. 18, 6211–6220).

1.8 Isolation of Mitochondria and S-100 Fraction

Mitochondria were isolated using a modification of the method described by Yang et al., 1997, Science 275: 1129. Briefly, $20\times10^6$ cells were IL-4 stimulated or deprived, harvested, and washed with ice-cold PBS. Cell pellet was suspended in 5 vol. ice-cold buffer A (20 Mm HEPES-KOH (pH 7.5), 10 mM KCl, 1.5 mM $MgCl_2$, 1 mM EDTA, 1 mM EGTA, 1 mM DTT, 0.1 mM PMSF, and 250 mM sucrose) supplemented with protease inhibitors. Cells were disrupted in a Dounce homogenizer (Kontes, Vineland, N.J.), the nucleic were centrifuged ($1.000\times g$, 10 min. $4°$ C.), and the supernatant was further centrifuged ($1.000\times g$. 15 min., $4°$ C.). The resulting mitochondrial pellet was resuspended in buffer A and stored at $-80°$ C. The supernatant was centrifuged ($100,000\times g$, 1 h, $4°$ C.), and the resulting S-100 fraction was stored at $-80°$ C.

2. Results

2.1 Bad Associates with Lipid Rafts in IL-4-Stimulated Cells

It has been shown that after IL-3-stimulation, Bad becomes phosphorylated, resulting in association to 14-3-3 protein. More recently, ti has been shown that IL-2 induces Bad phosphorylation, but not association with 14-3-3 protein (Ayllón et al., 2001, J. Immunol. 166, 7345–7352). FIG. 1 shows that neither IL-4-stimulation nor IL-4-deprivation results in association of Bad to 14-3-3 protein. As internal control, the interaction of Raf and the 14-3-3 protein is shown (FIG. 1).

Figure 2A:
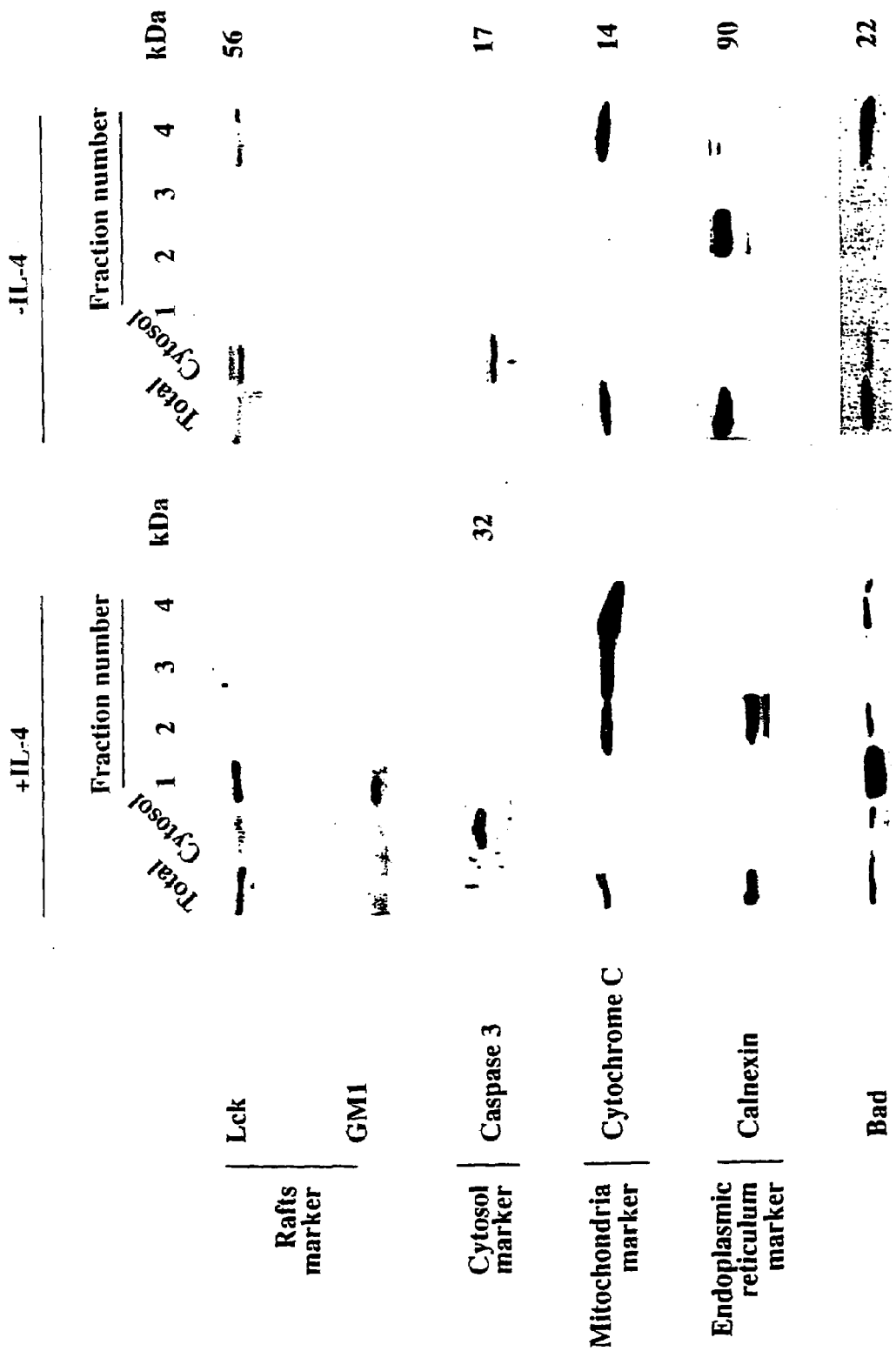

The subcellular distribution of Bad in IL-4-stimulated or -deprived cells has been analyzed. IL-4-stimulated or -deprived cells were lysed and fractionated over sucrose gradient. To validate the gradient protocol, fractions (1 to 4) were immunoblotted with markers for rafts (Lck and GM1 ganglioside), mitochondria (cytochrome C), endoplasmic reticulum (calnexin) and cytosol (caspase 3). Nuclear fraction (fraction 5) is not shown in the blot because there is not Bad localization in the nucleus. Rafts were detected by western blot in fraction 1 using anti-Lck antibody and CTx-Biotin, which recognizes GM1 ganglioside (FIG. 2A). Most of Bad was found in rafts (fraction 1), although a very small fraction was also present in mitochondria (fraction 4), cytosol and endoplasmic reticulum (fraction 2). As internal control, Bad was observed in total extracts of IL-4-stimulated cells. Finally, it has been observed that the fraction of Bad that is sequestered in lipid rafts is dephbsphorylated.

It has been previously reported that Bcl-2 is expressed in IL-2-stimulated cells and Bcl-$x_L$ in IL-4 cultured cells (Gomez, J. et al, 1998, Oncogene 17: 1235). When IL-4-maintained cells are deprived of lymphokine, they undergo apoptosis. As early as 4 h after IL-4 deprivation, ≈9% of the cells were apoptotic, reaching 40% at 24 h, whereas control IL-4-stimulated cells showed no significant level of apoptosis.

Figure 2B:
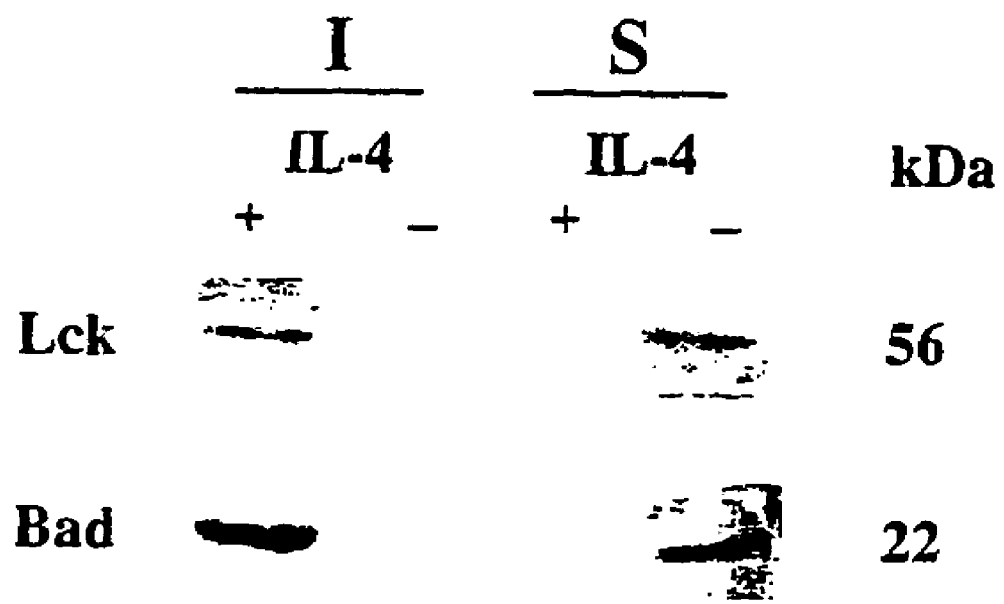

IL-4-deprivation induces disorganization of rafts (fraction 1), which are not detected using either anti-Lck antibody or CTx-Biotin. The mitochondria marker, which also contains other cellular structures with similar density, is observed in fraction 4 and most of the caspase 3 is cleaved, given a new protein of lower molecular weight. More interesting, Bad is almost undetectable in cytosol and rafts are only observed in fraction 4, which corresponds to mitochondria and cellular structures with similar density (FIG. 2A). This result strongly suggests an IL-4-dependent association of Bad with rafts and translocation to mitochondria upon IL-4-deprivation. Rafts were also isolated by Triton X-100 flotation gradient. As shown in FIG. 2B, Bad and Lck are detected in the detergent insoluble fraction (I) of IL-4-stimulated cells, which corresponds to lipid rafts. In IL-4-deprived cells, Bad and Lck are detected in the fraction corresponding to soluble proteins (S). It has been observed that post-translational myristoylation targets Bad to rafts (data not shown).

The subcellular localization of Bad was also analyzed in mitochondrial and cytosolic fractions of IL-4-stimulated or deprived cells. Bad was detected in the mitochondrial fraction of IL-4-stimulated cells. The amount of Bad associated with mitochondria increased upon IL-4-deprivation. Traces of Bad were detected in the cytosolic fraction of IL-4-stimulated or -deprived cells. The antiapoptotic molecule Bcl-$x_L$ was weakly detected in the mitochondrial fraction of IL-4-stimulated cells, increasing after IL-4 deprivation. As an internal control of protein fractionation, the blot was probed with anti-caspase 3 (cytosolic marker), anti-mitochondria Mito 2813 (pyruvate dehydrogenase, mitochondrial marker), and anti-calnexin to show the lack of endoplasmic reticulum contamination in mitochondrial preparation. Total extracts (late T) were used as a positive control of calnexin expression. Finally, the association of Bad with some Bcl-2 family members was explored. Coimmunoprecipitation experiments of cytoplasmic proteins under IL-4 stimulation or deprivation conditions using specific antibodies were performed. Bad was detected by Western blot in anti-Bcl-$x_L$ immunoprecipitates of IL-4 stimulated cells, decreasing throughout the starvation period analyzed. Probing the membrane with anti-Bcl-$x_L$ antibodies showed similar levels in all analyzed conditions.

Bad association to rafts in IL-4-stimulated cells was also analyzed in intact cells by confocal microscopy (FIG. 3A). IL-4-stimulated or -deprived cells were incubated with the raft marker cholera toxin B subunit (CTx-FITC) before secondary labelling with anti-Bad or anti-Lck antibody. Double immunofluorescence analysis with anti-Bad and CTx-FITC showed raft localization of Bad in the surface of IL-4-stimulated cells. In marked contrast, a disorganization of rafts in IL-4-deprived cells was observed and consequently, no rafts localization of Bad in IL-4-deprived cells (FIG. 3A). Double immunofluorescence analysis with anti-Lck and CTx-FITC was used as a positive control of localization of Lck in membrane rafts of IL-4-stimulated cells. Lck associated with rafts was not detected in IL-4-deprived cells (FIG. 3A).

The profile of green and red fluorescence colocalization was analyzed using the quantification software of Leica (TCS NT; Leica, Rockleigh, N.J.). A high number of green and red colocalization peaks was observed in the membrane of IL-4 stimulated cells stained with CTx-Lck or CTx-Bad. On the contrary, the level of colocalization of green and red fluorescence was strongly reduced in IL-4-deprived cells.

This result suggests that Bad is preferentially localized in lipid rafts in IL-4-stimulated cells and segregates from plasma membrane in IL-4-deprived cells.

Similar results of colocalization of Bad with lipid rafts were observed using freshly isolated thymocytes from mice.

Figure 3B:
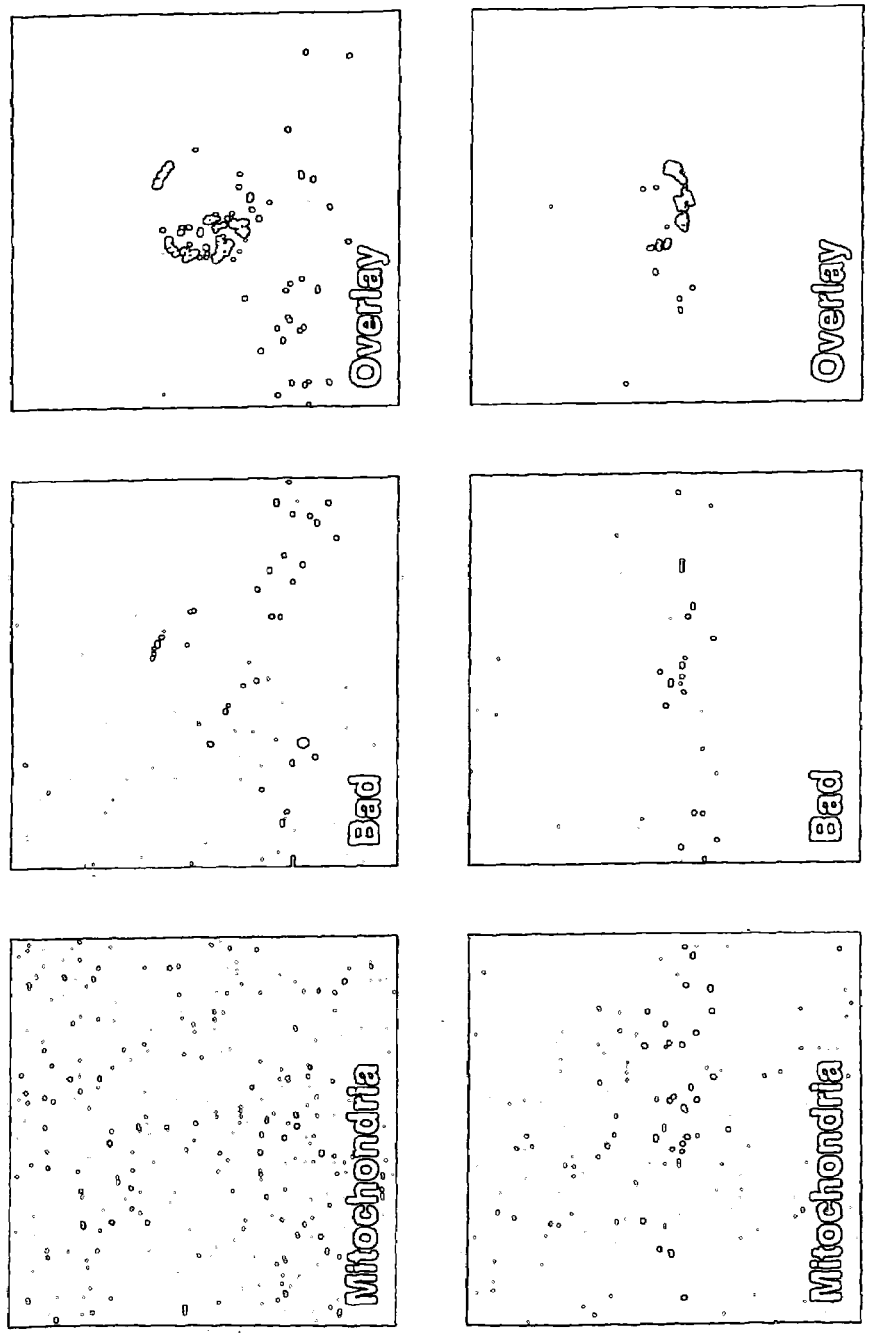

Bad association with mitochondria in IL-4-deprived cells was also analyzed in intact cells by confocal microscopy (FIG. 3B). Double immunofluorescence analysis with anti-Bad and anti-mitochondria antibodies shows weak association of Bad to mitochondria in IL-4-stimulated cells while there is a high fraction of Bad associated to mitochondria in IL-4-deprived cells (FIG. 3B). This separation of Bad from rafts correlates with its translocation to mitochondria in IL-4-deprived cells, as shown by cellular fractionation and confocal microscopy (FIGS. 2A and 2B).

The profile of green and red fluorescence colocalization was also analyzed using quantification software (Leica) and showed moderate green and red colocalization peaks in IL-4-stimulated cells stained with anti-Bad and anti-mitochondria Abs. The level of colocalization of both fluorescences strongly increased in IL-4 deprived cells.

2.2 Association of Bad to Lipid Rafts is Required for Prevention of Apoptosis

Depletion of cellular cholesterol impairs the ability of glycosyl phosphatidylinositol (GPI)-anchored proteins to associate with lipid rafts. To examine whether there is a similar requirement of cholesterol for the association of Bad with rafts, IL-4-stimulated cells were treated for 30 min with or without 10 mM methyl-β-cyclodextrin (M-β-CD) in serum-free medium to deplete cellular cholesterol. Cells were then incubated with CTx-FITC and labeled with anti-Bad or anti-Lck antibodies. Serum depletion alone weakly disrupt the association of Lck or Bad to lipid rafts (FIG. 4A). However, M-β-CD treatment causes a severe disruption of raft formation and association of Lck and Bad with rafts in IL-4-stimulated cells (FIG. 4A). This result indicates that disruption of raft formation by cholesterol depletion induces segregation of Bad and Lck from rafts in IL-4-stimulated cells.

Figure 4B:
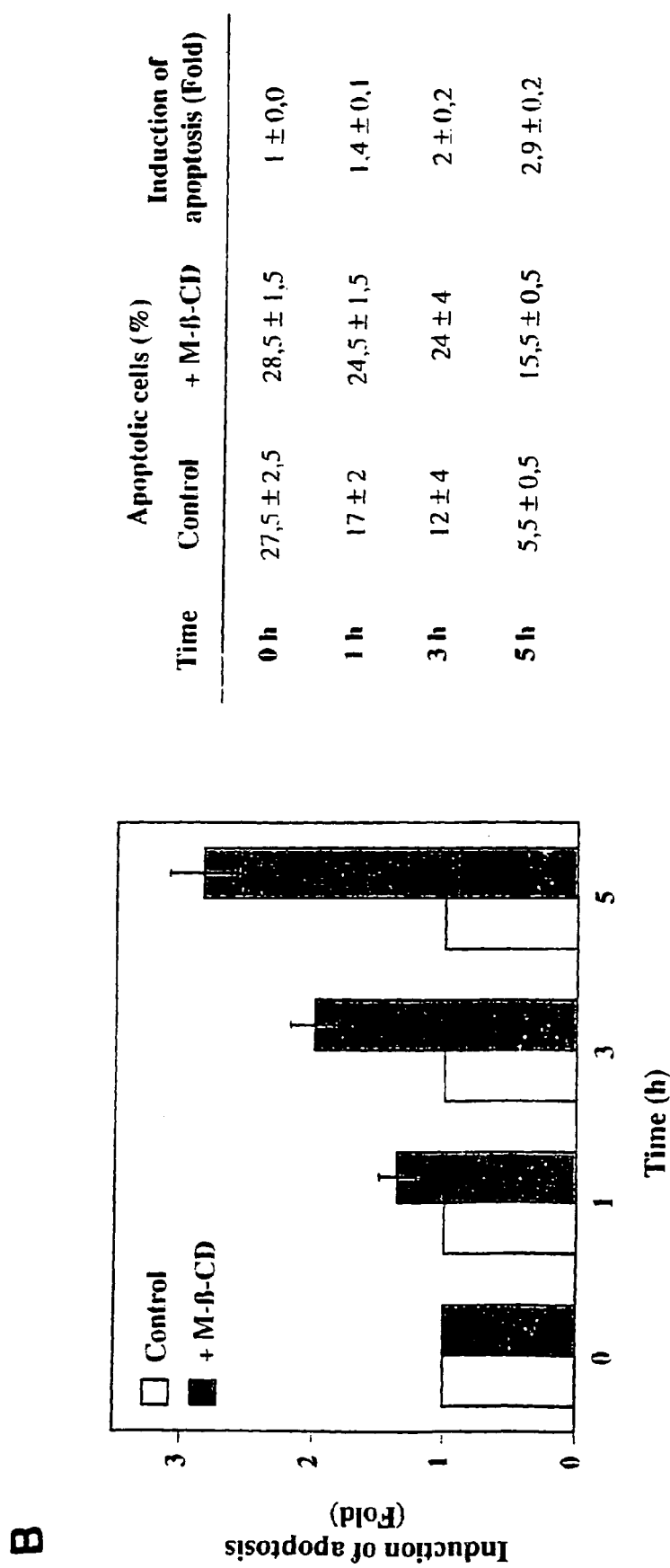

Given that exclusion of Bad from rafts was also observed in apoptotic IL-4-deprived cells (FIG. 3A), it was analyzed whether Bad association to rafts and its integrity was necessary for prevention of apoptosis. For this purpose, IL-4-stimulated cells were treated for 30 min with or without M-β-CD in serum-free medium, then washed, resuspended in IL-4-supplemented complete medium and analyzed for induction of apoptosis at different times (FIG. 4B). M-β-CD treated cells showed stronger level of apoptosis compared with control non treated cells, reaching the highest level 5 hours after M-β-CD treatment. Eight hours upon treatment, the amount of apoptotic cells detected in treated and non treated cells were similar because addition of serum restores the lipid composition of the membrane.

This result suggests that segregation of Bad from rafts is involved in the induction of apoptosis. Posttranslational modifications of Bad such as phosphorylation, and its role in Bad localization in rafts or mitochondria was further analyzed. FIG. 5A shows that IL-4 induces serine 136 phosphorylation of Bad, but not serine 112 and 155. Moreover, IL-4-deprivation induces serine 136 dephosphorylation of Bad. Given that IL-4 induces serine 136 phosphorylation of Bad, western blot was reprobed from FIG. 2A with anti-Bad serine 136 antibody. FIG. 5B shows that while most of Bad is localized in rafts in IL-4-stimulated cells, only the weak cytosolic fraction of Bad is serine 136 phosphorylated. In IL-4-deprived cells, traces of serine 136 phosphorylation are observed in cytosol and mitochondria. This result suggests that dephosphorylated Bad is sequestered in rafts and IL-4-deprivation induces segregation and translocation to mitochondria.

Subcellular localization of Bad enables to discover how Bad function may be regulated by dynamic interaction with lipid rafts or mitochondria. The distinct Bad distribution and function is directly related to IL-4-stimulation or -deprivation of the cells.

These data show that 14-3-3 protein does not control the proapoptotic role of Bad, contrary to previous reports. On the basis of this result, the subcellular distribution of Bad in IL-4-stimulated or -deprived cells was analyzed. These results show that different plasma membrane fractions can be separated using subcellular fractionation sucrose ultracentrifugation gradient because raft markers were successfully resolved from non-rafts markers. Rafts and mitochondria were also isolated by Triton X-100 flotation gradient and differential centrifugations, respectively. There are precedents for reversible raft association as has been shown following the movement of single fluorescence lipid molecules (Schutz et al., 2000, EMBO J. 19, 892–901). In addition, after activation by ligand binding, the epidermal growth factor migrates out of rafts into bulk plasma membrane (Mineo et al., 1999, J. Biol. Chem. 274, 30636–30643). The association of proteins with lipid rafts can be modulated because some proteins may be excluded from rafts by association to other proteins (Field et al., 1995, Proc. Nat. Acad. Sci. USA. 92, 9201–9205). Association of Bad with rafts may be involved in steps leading to Bad inactivation, because rafts do not constitute the final site of activation. IL-4-deprivation induces segregation of Bad from rafts. This results suggests a two steps apoptotic process: first, segregation of Bad from rafts, that triggers apoptosis and second, disorganization of lipid rafts during apoptotic process. This is strongly suggested by results showing that disruption of cholesterol rich rafts prevents Bad association and induces apoptosis in IL-4-stimulated M-β-CD-treated cells. Addition of fetal calf serum to IL-4-supplemented medium restores the lipid components of the plasma membrane, preventing progression of apoptosis.

Localization of proteins to distinct subcellular fractions is an essential step in multiple signaling pathways, including apoptosis. According to this, it has been shown that some signaling molecules are sequestered in rafts. Cholesterol depletion disrupts lipid rafts and modulates the activity of multiple signaling pathways in T lymphocytes (Kabouridis et al., 2000, Eur. J. Immunol. 30, 954–963). These results strongly suggest that in the absence of association of Bad to 14-3-3 protein, Bad is sequestered in rafts, avoiding a proapoptotic role and association with partners. IL-4 deprivation-induced segregation of Bad from rafts correlates with translocation to mitochondria and induction of apoptosis. Restriction of intermolecular interactions by sequestration in lipid rafts has been also described fro the α-chain of the IL-2R, avoiding its association with the β- and γ-chains of the IL-2R (Marmor, M; and M. Julius, 2001, Blood 98:1489). It is interesting to notice that in IL-4-stimulated cells, most of cellular Bad localizes in rafts in a dephosphorylated condition while the weak cytosolic fraction is serine 136 phosphorylated. These results show for the first time the sequestration of a pro-apoptotic protein into lipid rafts as a mechanism that controls the availability of said proapoptotic protein.

The invention claimed is:

1. A method of screening cellular polypeptides for pro-apoptotic or anti-apoptotic activity in a cell of a particular cell-type, said method comprising
   a. culturing cells of said particular cell-type under non apoptotic conditions and culturing cells of said particular cell-type under apoptotic conditions; and,
   b. detennining subcellular localisation of said cellular polypeptides in the cultured cells;
   wherein a localization of a cellular polypeptide in lipid rafts in cultured cells under non apoptotic conditions and a segregation of said cellular polypeptide from lipid rafts in cultured cells under apoptotic conditions is indicative that said cellular polypeptide has a pro-apoptotic or an anti-apoptotic activity in said particular cell-type, and
   wherein said screened cellular polypeptides belong to the Bcl-2 family and their subcellular localisation is determined by the use of a molecule which specifically recognizes a BH domain.

2. The method of claim 1, wherein said screened cellular polypeptides are isolated from biochemically isolated lipid rafts of said cells cultured in non apoptotic conditions by the use of a molecule which specifically recognizes a BH domain.

3. The method of claim 1, wherein said screened cellular polypeptides are further isolated by the use of a molecule which specifically recognizes a mirystoylated polypeptide.

4. The method according to claim 1, wherein said cell-type is characterized by the production of Bad protein (Bad$^+$ cell type).

5. The method according to claim 4, wherein said screened cellular polypeptides are isolated from biochemically isolated lipid rafts of said cells cultured under non apoptotic conditions and selected among the cellular polypeptides which physically interact with the Bad protein.

6. The method according to claim 2, wherein said BH domain is the BH4 domain.

7. The method according to claim 2, wherein said BH domain is the BH3 domain.

8. The method of claim 1, wherein said cells are mammalian cells.

9. The method of claim 1, wherein said non apoptotic conditions are proliferative conditions.

10. The method according to claim 1, wherein said cell-type is composed of cells of the immune system.

11. The method according to claim 1, wherein said cell-type is T cell lines.

12. The method of claim 2, wherein said screened cellular polypeptides are further isolated by the use of a molecule which specifically recognizes a mirystoylated polypeptide.

13. The method according to claim 2, wherein said cell-type is characterized by the production of Bad protein (Bad$^+$ cell type).

14. The method according to claim 2, wherein said cell-type is composed of cells of the immune system.

15. The method according to claim 2, wherein said cell-type is T cell lines.

16. The method according to claim 13, wherein said screened cellular polypeptides are isolated from biochemically isolated lipid rafts of said cells cultured under non apoptotic conditions and selected among the cellular polypeptides which physically interact with the Bad protein.

17. The method of claim 2, wherein said cells are mammalian cells.

18. The method of claim 2, wherein said non apoptotic conditions are proliferative conditions.

* * * * *

UNITED STATES PATENT AND TRADEMARK OFFICE
CERTIFICATE OF CORRECTION

PATENT NO. : 7,217,534 B2
APPLICATION NO. : 11/140275
DATED : May 15, 2007
INVENTOR(S) : Garcia et al.

It is certified that error appears in the above-identified patent and that said Letters Patent is hereby corrected as shown below:

On the title page, Item (73), the third assignee's name is incorrect. Item (73) should read:

-- (73) Assingees: Institut Pasteur, Paris (FR); Consejo Superior de Investigaciones Cientificas, Madrid (ES); Centre National de la Recherche Scientifique, Paris (FR) --

Signed and Sealed this

Third Day of July, 2007

JON W. DUDAS
*Director of the United States Patent and Trademark Office*